and Date of Patent: Feb. 20, 1990
United States Patent [19]
Shinn

[11] Patent Number: 4,902,121
[45] Date of Patent: Feb. 20, 1990

[54] RANGE DETECTOR FOR EYE INSTRUMENT HAVING INTERROGATING BEAM

[75] Inventor: Alan L. Shinn, Berkeley, Calif.

[73] Assignee: Allergan Humphrey, San Leandro, Calif.

[21] Appl. No.: 253,005

[22] Filed: Oct. 4, 1988

[51] Int. Cl.$^4$ ............................................... A61B 3/14
[52] U.S. Cl. ..................................... 351/208; 351/210
[58] Field of Search ................. 351/205, 211, 208, 210

[56] References Cited

U.S. PATENT DOCUMENTS

| | | | |
|---|---|---|---|
| 4,365,872 | 12/1982 | Nunokawa | 351/208 |
| 4,407,572 | 10/1983 | Humphrey | |
| 4,436,389 | 3/1984 | Sano | 351/208 |
| 4,511,227 | 4/1985 | Nunokawa et al. | 351/208 |
| 4,560,259 | 12/1985 | Humphrey | |
| 4,678,297 | 7/1987 | Ishikawa et al. | 351/208 |
| 4,732,466 | 3/1988 | Humphrey | |

Primary Examiner—P. M. Dzierzynski
Attorney, Agent, or Firm—Townsend and Townsend

[57] ABSTRACT

In an instrument having an interrogating optical beam for the measurement of various optical properties of the eye, a detector is disclosed for triangulating the towards and away distance of the eye from the objective of the measurement equipment thus utilizing the beam for serendipitous purpose of ranging. A photosensitive detector having two photosensitive elements is placed in a plane which includes the optical axis of the interrogating instrument and the detector. The detector is mounted towards the eye with the division between the two photosensitive surfaces normal to the plane including the interrogating optical beam and the detector. Typically, the detector has line of sight off axis with respect to the interrogating beam and intersects the axis at the preferred position for eye placement. An imaging lens relays a conjugate image of the detector to that point in space on the optic axis in front of the eye where ultimate placement of the eye for measurement is desired. By the simple expedient of moving servomotor to obtain a quality of signal between the photosensitive portions of the detector, rapid positioning of the eye can occur.

2 Claims, 1 Drawing Sheet

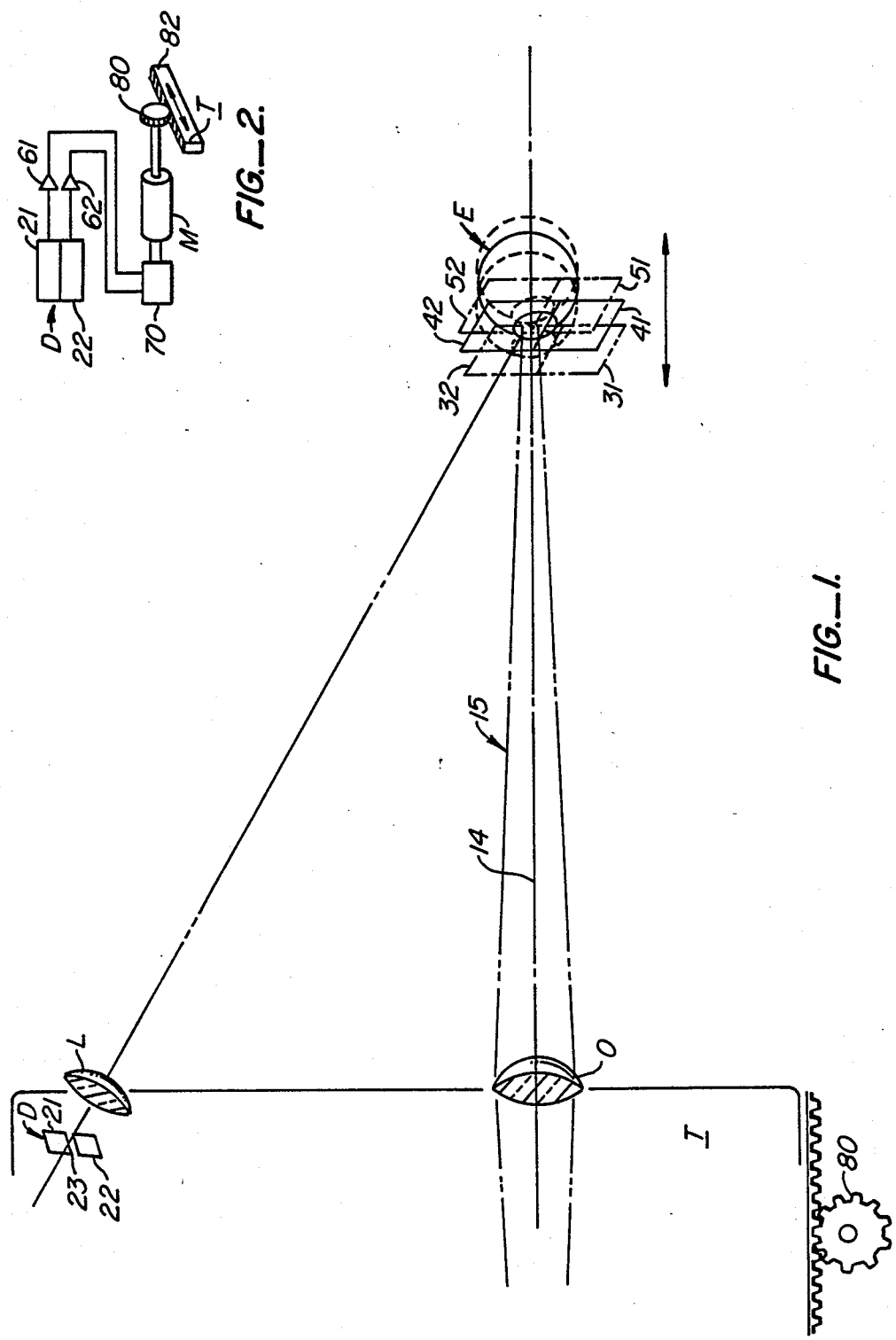

RANGE DETECTOR FOR EYE INSTRUMENT HAVING INTERROGATING BEAM

This invention relates to automated optical instruments emanating interrogating beams for determining the property of the eye. More particularly, an improved detector is shown for triangulating the distance to the eye and enabling rapid positioning of the eye in distance from the instrument.

BACKGROUND AND SUMMARY OF THE PRIOR ART

Many optical instruments are known which interrogate the eye with beams of light for determining the optical properties of the eye. Almost all of such instruments require accurate towards and away positioning of the eye from the instrument itself. That is to say the eye must be located at a precise distance from the objective of the interrogating instrument for the interrogating beam to make accurate measurement. Placement of the eye either too close to or too far away from the instrument renders an unreliable optical reading.

Examples of such instruments are disclosed in Humphrey U.S. Pat. No. 4,407,572 entitled Keratometer issued June 12. 1980; Humphrey U.S. Pat. No. 4,560,259 entitled Objective Refractor for the Eye issued Dec. 24, 1985; and Humphrey U.S. Pat. No. 4,732,466 entitled Fundus Camera issued Apr. 4, 1988.

Many of these instruments include possible schemes for determining the towards and away range of the eye along the interrogating axis. However, such schemes lack the overall reliability and simplicity needed for rapid ranging of the eye. Since the instruments attempt to determine the distance to the eye from interrogation parallel to the interrogating light, accuracy has been hard to obtain.

SUMMARY OF THE INVENTION

In an instrument having an interrogating optical beam for the measurement of various optical properties of the eye, a detector is disclosed for triangulating the towards and away distance of the eye from the objective of the measurement equipment thus utilizing the beam for serendipitous purpose of ranging. A photosensitive detector having two photosensitive elements is placed in a plane which includes the optical axis of the interrogating instrument and the detector. The detector is mounted towards the eye with the division between the two photosensitive surfaces normal to the plane including the interrogating optical beam and the detector. Typically, the detector has line of sight off axis with respect to the interrogating beam and intersects the axis at the preferred position for eye placement. An imagining lens relays a conjugate image of the detector to that point in space on the optic axis in front of the eye where ultimate placement of the eye for measurement is desired. By the simple expedient of moving servomotor to obtain a quality of signal between the photosensitive portions of the detector rapid positioning of the eye can occur.

An advantage of the disclosed invention is that it can be readily used in the infrared. Moreover, the invention can be used in modulated light so as to effectively ignore all light sources on the eye other than modulated interrogating beams emanating from the interrogating instrument.

BRIEF DESCRIPTION OF THE DRAWINGS

Other objects and features of this invention will become more apparent after referring to the following drawings in which:

FIG. 1 is a side elevation schematic showing an instrument emanating an interrogating beam from an objective along an optical axis with the detector of this invention looking along an intersecting axis and having the conjugate image of the detector projected to an eye for locating the optimal distance of the eye from the objective; and FIG. 2 is an electrical schematic illustrating the receipt of modulated light at the sections of the detector and the use of the signal to position the instrument in towards and away movement from the eye.

Referring to FIG. 1, an interrogating instrument I is schematically shown. The interrogating instrument includes a beam of typically infrared light 15 centered to an interrogating axis 14. Beam 15 proceeds from a source (not shown) through an objective O in the instrument outwardly in space.

The instrument I examines an eye E. It examines the eye E for various optical properties. These optical properties can include both the keratometry of the eye as well as a subjective examination of the optical prescription for the eye.

In such instruments, especially those instruments described in the prior art patents it has been found necessary to precisely position the eye E in its towards and away distance from the instrument I at objective O. If the eye is out of position with respect to the instrument, inaccurate readings can occur.

It will be understood that it is a simple matter for the routine to center beam 15 on the eye E. What is difficult is to obtain the precise towards and away positioning.

To this end there is placed a detector D. Detector D has two photosensitive surfaces 21, 22 with a linear boundary 23 therebetween.

The detector is mounted in a plane that includes optical axis 14 and the detector D itself. The division 23 between the photosensitive segments 21, 22 is aligned normal to the plane including the optical axis 14 and the detector D.

A conjugate image of the detector is projected by lens L to the desired position of eye E along the optical axis 14. Such a position is shown by the broken line on the detector image 41, 42. When an eye is located in the plane of the conjugate image 41, 42, a beam 14 projected onto the eye will appear between the two detector segments. Consequently, electrical signal at photosensitive segment 21 will equal electrical signal at photosensitive segment 22.

Presuming that eye E moves forwardly and towards the instrument I and its objective O, beam 15 projected from the instrument I will be projected so that conjugate image of the detector is coincident to the lower photosensitive portion. The conjugate photosensitive portion is illustrated at 31 and corresponds to segment 21. Little or no signal will be received at photosensitive segment 22.

Likewise, and if the eye is too far away from the instrument I and objective O, the beam of light projected to the eye will be coincident to the conjugate upper photosensitive portion 52. When the conjugate is relayed, the signal present on photosensitive surface 22 will predominate over the signal on photosensitive surface 21.

It can thus be seen that when the eye is too close, photosensitive surface 21 will receive a predominance of signal. When the eye is too far away, photosensitive surface 22 will receive a predominance of signal.

Utilization of this very simple signal can be best seen on FIG. 2. Each photosensitive segment connects through an amplifier 61, 62, which amplifier preferably amplifies only a discrete modulation frequency of beam 15. By this selective amplification, stray light or noise can be screened from the signal.

The output of the tuned amplifier 61, 62 passes to a differential amplifier 70. Dependent upon the strength of the respective inputs, differential amplifier 70 operates to drive the motor M in one or the other of two directions. Motor M through a pinion 80 drives a rack 82 attached to the instrument I. The instrument thus moves towards and away from the eye E responsive to the signals on the two photosensitive segments 21, 22.

It can thus be seen that the disclosed device solves a needed problem. That needed problem is the precision locating of an eye E with respect to an interrogating instrument I and its objective O in towards and away distance.

I claim:

1. In an optical instrument emanating an interrogating optical beam along an instrument axis with respect to an instrument objective, said interrogating optical beam being utilized by the instrument to interrogate, interpret and permit the recordation of the optical properties of an eye through attached sensor apparatus, an apparatus for ranging the eye with respect to the instrument objective utilizing the interrogating optical beam for a serendipitous ranging function comprising:

a detector having at least two photosensitive surfaces with a boundary therebetween;

said detector placed off axis with respect to said instrument axis:

said detector positioned with said photosensitive surfaces being directed towards said interrogating beam and the boundary between said surfaces being normal to a plane including the instrument axis and said detector:

a relay lens for relaying a conjugate image of said detector to a position along the axis of said interrogating beam in the vicinity of the eye being examined and forming an image of said detector at the distance from the objective of said instrument where positioning of the eye to be interrogated is desired; and means for detecting a signal between the photosensitive surfaces of said detector whereby towards and away positioning of said instrument relative to said eye occurs.

2. The invention of claim 1 and wherein said interrogating optical beam is modulated and said detecting includes means for detecting said modulated interrogating optical beam only.

* * * * *